United States Patent [19]

Andress

[11] Patent Number: 5,671,265
[45] Date of Patent: Sep. 23, 1997

[54] EVIDENTIAL RECONSTRUCTION OF VESSEL TREES FROM X-RAY ANGIOGRAMS WITH A DYNAMIC CONTRAST BOLUS

[75] Inventor: Keith Michael Andress, Plainsboro, N.J.

[73] Assignee: Siemens Corporate Research, Inc., Princeton, N.J.

[21] Appl. No.: 502,353

[22] Filed: Jul. 14, 1995

[51] Int. Cl.$^6$ .................................................. A61B 6/03
[52] U.S. Cl. ...................................... 378/98.11; 378/98.12
[58] Field of Search .................................... 378/62, 98.11, 378/98.12, 98, 901, 4, 98.2; 364/413.13–413.16, 413.23

[56] References Cited

U.S. PATENT DOCUMENTS 4,943,987  7/1990  Asashina et al. ................... 378/98.12

Primary Examiner—Don Wong
Attorney, Agent, or Firm—Donald B. Paschburg

[57] ABSTRACT

A three dimensional reconstruction of vessel trees from rotational digital subtraction angiogram sequences is described. The goal of the process is to estimate the probability that each voxel contains a vessel using the projection data. The system utilizes x-ray angiographic equipment capable of producing rotational digital subtraction angiogram sequences. Reconstruction of the geometry of the vasculature is based on the projection images. The reconstructed geometry is then displayed on a screen or used for measuring specific physiological parameters. The Dempster-Shafer theory of evidence is used to combine information about location of the vessels from the different projections contained in the digital subtraction angiogram sequence.

20 Claims, 4 Drawing Sheets

$$w_{ij} = \frac{\text{AREA OF TRIANGLE}}{\text{AREA OF PIXEL}}$$

EVIDENTIAL RECONSTRUCTION OF VESSEL TREES FROM X-RAY ANGIOGRAMS WITH A DYNAMIC CONTRAST BOLUS

BACKGROUND OF THE INVENTION

1. Field of the Invention

The present invention relates to reconstruction of vessel trees and more particularly to a new voxel-based system of reconstructing three dimensional vessel trees based on rotational digital subtraction angiogram data with a dynamic bolus.

2. Description of the Prior Art

The three dimensional reconstruction of vessel trees has a number of potential clinical applications. Digital subtraction angiogram (DSA) sequences are often used by both neurosurgeons and interventional radiologists in the treatment of aneurysms. Neurosurgeons use the sequences during surgery planning to visualize the relationship between the aneurysm and its surrounding vessels to determine if it is possible to clip the neck of the aneurysm. Unfortunately, it is sometimes difficult to determine the relationship between the aneurysm and the surrounding vessels from the views contained in the DSA sequence. It is thought that a three dimensional representation of the vessel tree would aid this visualization process because it would allow the vessel tree to be rendered from arbitrary viewpoints. Interventional radiologists treating aneurysms and arterial-venous malformations have the same need for visualization of the vessel tree.

The problem of reconstructing a three dimensional representation of a section of the vessel tree from multiple X-ray angiograms has received a great deal of attention in the past. One approach to this problem assumes a parametric representation of the vessel tree. Typical methods using this approach attempt to represent the vasculature via its skeleton and the local cross sections of its vessel branches. This type of reconstruction may be applicable in situations in which there is some movement of the vessel bed because it may be possible to model the variation of the parameters over the range of motion. Pope, D. L., van Bree, R. E., Parker, D. L., "Cine 3-D Reconstruction of Moving Coronary Arteries from DSA Images", Computers in Cardiology, 1986; Parker, D. L., Pope, D. L., van Bree, R. E., and Marshall, H. W., "Three Dimensional Reconstruction of Moving Arterial Beads Form Digital Subtraction Angiography", Comp. and Biomed Res., Vol. 20, 1987. Due to the vessel segmentation, matching and parameter estimation they require, these methods are most appropriate in the reconstruction of vessel trees of limited complexity. These techniques also break down when they encounter pathologies in which the vessel shapes do not fit the selected model.

Other reconstruction techniques do not attempt to model the vessel tree parametrically. Instead, they reconstruct the scene using a voxel-based representation. These techniques descend directly from classical reconstruction techniques. Rougee, A., Hanson, K. M., and Saint-Felix, D., "Comparison of 3D Tomographic Algorithms for Vascular Reconstruction", SPIE Medical Imaging II, 1988. Because these vessel reconstruction methods are fundamentally cone-beam reconstruction techniques, their computational load is a major concern.

A number of clinical X-ray angiographic machines capable of producing rotational DSA sequences have been introduced recently. Rotational angiography is an imaging technique in which the X-ray source and image intensifier of an angiographic system are rotated around the patient as the image sequence is being acquired. Rotational DSA requires two passes. One pass is made as X-ray opaque contrast material is injected into the vasculature; the other is made without any contrast material. Subtracting the corresponding images from the two sequences theoretically yields a sequence in which only the vessels containing the contrast material are present. This sampling geometry is exactly that used by many cone-beam reconstruction techniques. Smith, B. D., "Cone-beam Tomography: Recent Advances and a Tutorial Review", Optical Engineering, Vol 29, No. 5, 1990; Feldkamp, L. A., Davis, L. C., and Kress, J. W., "Practical Cone-beam Algorithm", J. Opt. Soc. Am., Vol. 1, No. 6, 1984. Ideally, one would like to have a DSA sequence in which all vessels are saturated with contrast material over the entire sequence. Unfortunately, due to physiological and machine limitations, it is impossible to keep the vessels saturated over an entire scan. The angiographic machines used to produce rotational DSAs are typically capable of acquiring a sequence over an arc of 90 to 180 degrees in approximately four seconds. Typically, such a sweep has 45 to 90 images. For neuroangiographic applications, the maximum injection time is limited to approximately six seconds due to toxicity of the contrast material. Furthermore, it takes approximately four seconds from the start of the injection until the contrast material completely fills the vessel tree. The combination of these constraints means that the vessel tree is saturated only for approximately two seconds, or one half of a scan. Thus, it is important that any reconstruction method be able to account for the dynamics of the contrast bolus as it evolves over the DSA sequence.

SUMMARY OF THE INVENTION

The present invention is a system of reconstructing a three dimensional representation of arterial structures from rotational DSA sequences. Three major aspects of the present invention are the reconstruction of the geometry of the vessels by estimating the probability of occupation over the voxel space rather than physical components. Conversion of projection values into evidence (probability estimate) and then backprojecting the evidence through the volume. And, third, the use of the Dempster-Shafer Theory to combine information from other sources.

The present invention comprises an acquisition component, a reconstruction component and a display/measurement component. The acquisition component utilizes x-ray angiographic equipment capable of producing rotational DSAs. The acquisition component acquires the mask series and the contrast series of the rotational DSA. Each of the mask images, which as a group comprise the mask series, is then subtracted from the corresponding contrast image to create a DSA sequence. In another embodiment of the present invention, the mask images can be estimated from the contrast images. In a third embodiment, the acquisition component would only utilize the contrast images.

The reconstruction component recreates the geometry of the vasculature based on the projection images gathered by the acquisition component. The geometry is represented by the rectangular lattice of voxels, each of which contains an estimate of the probability that a vessel passes through the region of anatomy to which the voxel corresponds. The reconstruction component starts by converting DSA images into belief functions. The belief volume is then initialized to indicate complete ignorance. The iterative procedure then starts with data being projected from the belief volume. Evidence images are backprojected and if a stop criteria is not met, the iterative procedure starts over.

The display measurement component renders the final belief volume using standard technology (e.g. volumetric rendering, maximum/minimum intensity projection, radiographic projection). The display/measurement component has several embodiments based on the clinical application of the present invention. One such embodiment is a system for displaying the volumetric data on a video screen. Another embodiment is a system for measuring specific physiological parameters from the volumetric data.

DETAILED DESCRIPTION OF THE INVENTION

Figure 1:
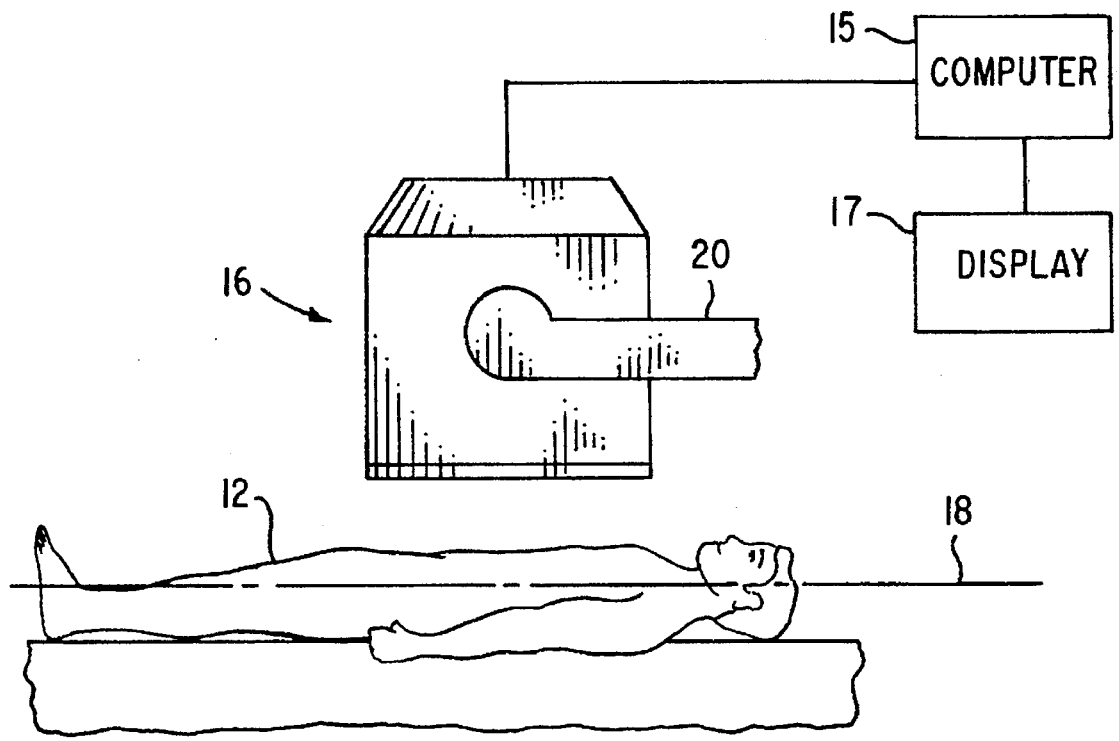
FIG. 1 illustrates one embodiment of the hardware of the present invention.

FIG. 1 illustrates a diagram of x-ray angiographic equipment capable of producing digital subtraction angiogram (DSA) sequences in accordance with the present invention. During the study, the camera 16 is rotated around the axis 18 of the patient 12 by a gantry 20. A frame of planar image data is acquired at each of a plurality of camera stops which are regularly spaced around the patient. The planar image data collected by the camera 16 is routed to a computer 15. Conventional x-ray angiographic reconstruction software is adapted to reconstruct three dimensional images along the axis 18. Images of the patient 12 may be displayed on a display 17.

The goal of classical reconstruction systems is the recovery of the numeric measure of some property of a material from multiple projections. These parameters include the coefficient of absorption for absorption tomography, rate of emission for emission tomography, index of refraction for diffraction tomography, etc. Thus, for the problem of reconstructing a vessel tree from digital subtraction angiogram (DSA) projections, one could try to reconstruct the coefficient of absorption (i.e. Haunsfield Units) over the volume. This information could then be used to determine the distribution of the contrast material within the vessels. Unfortunately, the dynamics of the contrast bolus in rotational DSA series violates one of the fundamental assumptions of all classical reconstruction techniques: all of the projections must be from the same object.

Fortunately, the clinical applications listed above do not require knowledge about the distribution of the contrast material within the vessels. Only the geometry of the tree is needed to allow it to be rendered. For this reason, there is no attempt to recover the coefficient of absorption over the volume; instead, the probability that each voxel is occupied by a vessel is made. At the end of the reconstruction process, voxels with a high probability associated with them are considered to contain a vessel.

If a pixel in a DSA frame contains a vessel, then the projection ray that falls on this pixel must cross at least one vessel in the volume. However, it is not known which voxel(s) along that line contain(s) the vessel(s). Therefore, the present invention increases the probabilities for all of the voxels that lie along the ray. Conversely for static scenes, the lack of a vessel in the projection also implies that the projection ray does not intersect any vessels in the volume. However, for dynamic scenes, this is not necessarily true because the projection ray may intersect a vessel that has not yet filled with contrast material. Therefore, the present invention may decrease the probability that there is a vessel for each of the voxels along the line; however, the present invention may not rule out this possibility entirely by setting each probability to zero. The system of estimating the probability that a voxel is occupied from multiple projections, the present invention, is called an evidential reconstruction technique (ERT) because the absence or presence of vessels in the projection images is used as evidence to update the voxel probabilities.

In order to describe the evidential reconstruction technique in detail, three components must be specified: 1) the method used to initialize the voxel probabilities 2) the method used to convert the pixel values in the images into evidence for each of the voxels along the pixels' projection ray and 3) the method used to update the voxels' probabilities given the new evidence. The present invention uses the Dempster-Shafer (D-S) theory of evidence as its uncertainty calculus. Therefore, each of the three components have been formulated to take advantage of properties of the D-S theory. For a detailed representation of the theory please see Shafer, G. "A Mathematical Theory of Evidence", Princeton University Press, 1976.

A brief introduction to the Dempster-Shafer Theory of Evidence follows. In a random experiment, the frame of discernment (FOD), $\Theta$, is the set of all possible outcomes. For example, if a die is rolled, $\Theta$ can represent the set of possibilities, "the number showing is i", where $1 \leq i \leq 6$; therefore, $\Theta$ may be defined as the set $\{1, 2, 3, 4, 5, 6\}$. The $2^{|\Theta|}$ subsets of $\Theta$ are called propositions. The power set of $\Theta$, denoted by $2^{\Theta}$, is the set of all the propositions. In the die example, the proposition "the number showing is even" would be represented by the set $\{2, 4, 6\}$. The members of a FOD are known as singleton propositions or merely singletons.

In the D-S theory, probability masses are assigned to propositions, (i.e. to the subsets of $\Theta$). The probability masses assigned to a subset, $\Psi$, of the FOD is a measure of the total belief committed exactly to $\Psi$. This belief cannot be further subdivided among the subsets of $\Psi$ and does not include the measures of belief committed to the subsets of $\Psi$. Thus, the mass assigned to $\Psi$ is constrained to stay within the subset but is free to move to any element of the subset.

Assigning a probability mass of value 1 to a subset of $\Theta$ represents complete certainty that the result of the experiment is one of the members of that subset. As the mass assigned to a subset decreases, this represents a decreasing amount of certainty that the result is one of the members of the subset. Assigning a mass of 0 to a strict subset of $\Theta$ represents complete uncertainty whether the outcome was one of the members of the subset. If no information is known about the outcome of an experiment, then all of the probability mass should be assigned to $\Theta$, which represents complete ignorance. In the example, assigning a probability mass to $\Theta$ is equivalent to the vacuous statement: "the number showing is one of $\{1, 2, 3, 4, 5, 6\}$".

The D-S method of attaching probability masses to subsets of $\Theta$ is a major departure from the Bayesian formalism in which probabilities must be assigned to the individual members of $\Theta$. For example, in the D-S theory, the probability mass assigned to $\Theta$ represents complete ignorance because the mass assigned to $\Theta$ may move to any element of the FOD. This explicit method of expressing ignorance is in contrast to what must be done using the Bayesian approach where each member of $\Theta$ would be assigned a probability of ⅙, because without any information, one must assume that each outcome is equally likely.

The probability masses assigned to the propositions must have unity sum. When a source of evidence assigns probability masses to the propositions discerned by $\Theta$, the resulting function is called a basic probability assignment (BPA). Formally, a BPA is function $m: 2^\Theta \to [0,1]$ where 1) $m(\emptyset) = 0$ 2) $0 \leq m(\Psi) \leq 1$  (1)

3)
$$\sum_{\Psi \subseteq \Theta} m(\Psi) = 1$$

For example, assume that there is evidence that an even number is showing on a die with degree 0.5 and there is evidence that the number showing is two with degree 0.4. Because these are the only two pieces of information available, the remaining mass, $1.0 - 0.5 - 0.4 = 0.1$, is assigned to $\Theta$ (which represents ignorance on the outcome of the experiment).

$$m(\{2,4,6\}) = 0.5$$
$$m(\{2\}) = 0.4 \quad (2)$$
$$m(\Theta) = 0.1$$

A subset, $\Psi$, of $\Theta$ is called a focal element of the belief function if $m(\Psi) \neq 0$.

A belief function, $Bel(\Psi)$, over $\Theta$ is defined by $$Bel(\Psi) = \sum_{y \subseteq \Psi} m(y) \quad (3)$$

In other words, the belief in a proposition $\Psi$ is the sum of probability masses assigned to all the propositions implied by $\Psi$.

Thus, $Bel(\Psi)$ is the measure of the belief in all subsets of $\Psi$, and not the amount allocated precisely to $\Psi$. Note that the belief in any singleton is equal to its probability mass. For example, using the above BPA, the belief that an even number is showing is $$Bel(\{2, 4, 6\}) = m(\{2, 4, 6\}) + m(\{2\}) = 0.5 + 0.4 = 0.9$$

Dempster's rule of combination, states that two BPAs with the same FOD, $m_1$ and $m_2$, corresponding to two independent sources of evidence may be combined to yield a new BPA, $m_{total}$, via $$m_{total}(\Psi) = K \sum_{\substack{\Psi_1, \Psi_2 \\ \Psi_1 \cap \Psi_2 = \Psi}} m_1(\Psi_1) m_2(\Psi_2) \quad (4)$$

where K does not depend on $\Psi$.

$$1/K = \sum_{\substack{\Psi_1, \Psi_2 \\ \Psi_1 \cap \Psi_2 = \emptyset}} m_1(\Psi_1) m_2(\Psi_2) \quad (5)$$

This formula is commonly called Dempster's rule or Dempster's orthogonal sum is denoted as $$m_{total} = m1 \oplus m2 \quad (6)$$

If $K^{-1}$ is equal to zero, then the two input belief functions are said to be completely contradictory and the result of the combination is not defined.

In the general case, Dempster's sum takes exponential time (in the size of the FOD) to combine evidence from two independent sources. This is shown easily by observing the formula for Dempster's sum. The main reason for the exponential complexity is the requirement that the probability mass for all $2^{|\Theta|}$ subsets of $\Theta$ be evaluated when combining evidence from independent sources. In the general case, it also is necessary to enumerate all $2^{|\Theta|}$ subsets of $\Theta$ when computing the belief of an arbitrary proposition from the BPA.

There are a number of special types of belief functions with significantly improved computational complexity. In general, these gain the computational advantage by restricting the size of the FOD or by restricting the focus of belief to a small number of subsets of $\Theta$. These belief functions exhibit certain properties that allow them to be combined efficiently.

A belief function with at most one focal element (not counting the entire FOD, $\Theta$) is called a simple support function. A separable support function is either a simple support function or is equal to the orthogonal sum of two or more simple support functions. One type of simple support function, a dichotomous belief function, is a belief function with focal elements $\{\Psi, \neg\Psi, \Theta\}$ for some subset $\Psi$ of $\Theta$. The BPAs from two dichotomous belief functions with identical focal elements, $\{\Psi, \neg\Psi, \Theta\}$ can be combined in constant time using the following formulas:

$$m_{total}(\Psi) = (m_1(\Psi) + m_2(\Psi) + m_1(\Psi) m_2(\Theta) m_1(\Theta) m_2(\Psi))/(1 - m_1(\Psi) m_2(\neg\Psi) - m_1(\neg\Psi) m_2(\Psi))$$

$$m_{total}(\neg\Psi) = (m_1(\neg\Psi) m_2(\neg\Psi) + m_1(\neg\Psi) m_2(\Theta) + m_1(\Theta) m_2(\neg\Psi))/(1 - m_1(\Psi) m_2(\neg\Psi) - m_1(\neg\Psi) m_2(\Psi)) \quad (7)$$

$$m_{total}(\Theta) = (m_1(\Theta) m_2(\Theta))/(1 - m_1(\Psi) m_2(\neg\Psi) - m_1(\neg\Psi) m_2(\Psi))$$

A belief function with a binary FOD ($|\Theta| = 2$), is a dichotomous belief function and can be combined efficiently; other properties of binary and dichotomous belief functions can be found in Safranek, R. J., Gottschlich, S., and Kak, A. C., "Evidence Accumulation Using Binary Frames Of Discernment For Verification Vision", IEEE Trans. Robotics and Automation, 1990. Only the simplest types of special forms of belief functions have been described here; more complex forms have also been investigated as described in Barnett, J. A., "Computational Methods For A Mathematical Theory of Evidence", Int'l Joint Conference on Artificial Intelligence, 1981; Shafer, G., and Logan, R. "Implementing Dempster's rule for hierarchical evidence", Artificial Intelligence, 1987.

As mentioned previously, the goal of the ERT of the present invention is to estimate the probability that each voxel contains a vessel. Thus, there are two possibilities for each voxel: either it contains a vessel or it doesn't. This can be represented in ERT by associating a belief function with every voxel in the reconstruction space. The two possible outcomes are represented as a binary FOD: $\Theta=\{occ, unocc\}$ to represent whether the voxel is occupied or unoccupied, respectively. We call the volume of voxels with associated belief functions a belief volume.

The BPA for the voxel belief functions are initialized such that $m(\Theta)=1$, i.e. complete ignorance. These belief functions are then updated by backprojecting evidence based on vessel structures in each projection and combining that evidence together using D-S theory.

A two step process is used to backproject the evidence. First, the pixel values are converted into a belief function in the projection space. For every pixel in the projection image, the belief function is meant to represent the probability that at least one vessel was projected onto that pixel. Currently, a simple function that maps grey scale values into positive evidence can be used. More sophisticated mapping functions may also use the pixel values in the local neighborhood. Note that this scheme does not require that the vessels be segmented in the projection images. Avoiding a segmentation step makes the conversion process robust with respect to noise because small variations in the grey scale values of the projections produce small variations in the evidence values.

A number of functions for converting grey scale values into evidence have been investigated. All of these functions are monotonically increasing functions of the ratio of a pixel value to the greatest pixel value. Assuming that pixel values represent absorption coefficients (i.e. vessels appear bright against a dark background), it is assumed that each projection image contains at least some vessels, and that there is a minimum of noise and misregistration artifacts in the DSA images. Therefore, it is reasonable to believe that the pixel with the greatest grey scale value is most likely to contain the projection of one or more vessels. Furthermore, as the grey scale values for pixels decrease, it seems reasonable to assume that the corresponding pixels are less likely to contain projections of vessels. The following function has been used to map grey scale values into positive evidence values:

$$pos(v) = \alpha + (1-\alpha)(v/v_{max})^\gamma \quad (8)$$

where $v$ is the pixel's grey scale value and $v_{max}$ is the maximum grey scale value in the image. The two parameters $\alpha$ and $\gamma$ affect how the normalized grey scale values map into evidence ($0 \leq \alpha \leq 1$). Note that the pos(v) function is constrained to be between 0 and 1; thus, it can be a valid probability mass. After the positive evidence has been generated, the projection's complete BPA is formed:

$$m_{projection}(\{occ\}) = pos(v)$$

$$m_{projection}(\{unocc\}) = 1 - pos(v) \quad (9)$$

$$m_{projection}(\Theta) = 0$$

The second step in the evidence backprojection process is the distribution of the evidence contained in the projection BPAs among the voxels in a pixel's projection ray. The distribution process "smears" the evidence along the ray such that the sum of the evidence given to the voxels that fall on the ray equals the BPA of the corresponding pixels in the projection images. The evidence is distributed in this manner because it is not known where along the length of the projection the vessels are intersected. This process is described in detail below.

Figure 2:
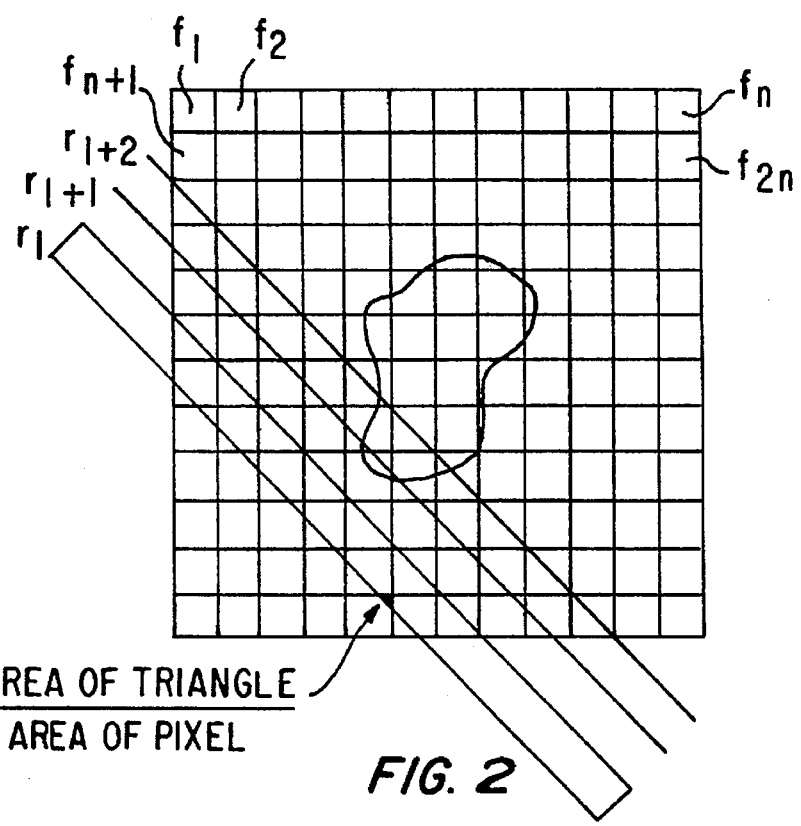
FIG. 2 illustrates a geometric model used to distribute evidence along a projection.

ART's projection model as described in Kak, A. C., and Slaney, M., "Principles of Computerized Tomographic Imaging", IEEE Press, 1988 can be adopted to distribute the evidence along the projection ray. In order to simplify the description of the model, its two dimensional definition can be utilized. The three dimensional definition is a trivial extension. The geometry used to define this model in two dimensions is shown in FIG. 2. In this figure, the value of pixel i is $f_i$ and the value of projection ray j is $r_j$. As shown here, the projection ray is assumed to have finite width. This width is constant for parallel-beam geometries and it increases as one moves from the X-ray source to the sensor face for fan-beam/cone-beam geometries (the parallel beam case is shown here). A projection is formed by integrating the image function over the area of support defined by the projection ray. Pixels are defined to have a rectangular cross section. Their value is assumed to be the mean value of the image function over this rectangular area.

In three dimensions, this geometry is equivalent to the intersection of a pyramid shaped projection sample with a cubic voxel. Due to the complex geometry of the intersection of these shapes, it is often computationally impractical to exactly compute the weights as described above. There are a number of techniques that can be used to approximate these values. 1) The volume covered by the pixel can be point sampled either on a regular grid or stochastically. The percent of the samples that lie within the projection ray is used as the estimate of the weight. 2) The reconstruction volume can be treated as a stack of slices and the weights computed so as to interpolate the value of the volume at the center of the projection ray. 3) The projection ray can be modeled as a cone and the voxels can be modeled as spheres. This produces a simpler intersection geometry that can be quickly computed from the distance of the voxel from the x-ray source and the distance of the voxel from the center of the projection ray. Other approximations are mentioned in the prior art.

For every pair of pixel, i, and projection ray, j, one can compute the fractional area (weight) of the pixel covered by the projection ray, $w_{ij}$, where:

$$w_{ij} = \text{area of triangle/area of pixel} \quad (10)$$

With this model, one can approximate the value of a projection via the following formula. The approximation becomes exact if one assumes that the image function is constant over the area covered by a pixel:

$$p_i = \sum_j w_{ij} f_j \quad (11)$$

Given the three dimensional equivalent of this imaging model, it is possible to distribute a projection's evidence to its contributing voxels by dividing the probability masses of the singletons proportionally to a voxel's weight. This distribution of evidence can be thought of as a backprojection process. Given the BPA of projection j, denoted by $m_{proj\ (j)}()$, the following formulas are used to determine the BPA of the voxels which were intersected by the projection. The BPA for voxel i, a voxel that was intersected by the projection, is denoted by $m_{voxel\ (i)}()$:

$$m_{voxel\ (i)}(\{occ\}) = m_{proj\ (j)}(\{occ\})\ (w_{ij}/\Sigma_k w_{kj})$$

$$m_{voxel\ (i)}(\{unocc\}) = m_{proj\ (j)}(\{unocc\})\ (w_{ij}/\Sigma_k w_{kj}) \quad (12)$$

$$m_{voxel\ (i)}(\Theta) = 1 - m_{voxel\ (i)}(\{occ\}) - m_{voxel\ (i)}(\{unocc\})$$

Since we are trying to determine the probability that a voxel contains a vessel, we say that voxel i has high belief if $m_{voxel\ (i)}(\{occupied\})$ is large (because the belief in a singleton is equal to its probability mass). Likewise, during the backprojection process, we call $m_{voxel\ (i)}(\{occupied\})$ the positive evidence and $m_{voxel\ (i)}(\{unoccupied\})$ the negative evidence from the projection.

Figure 3:
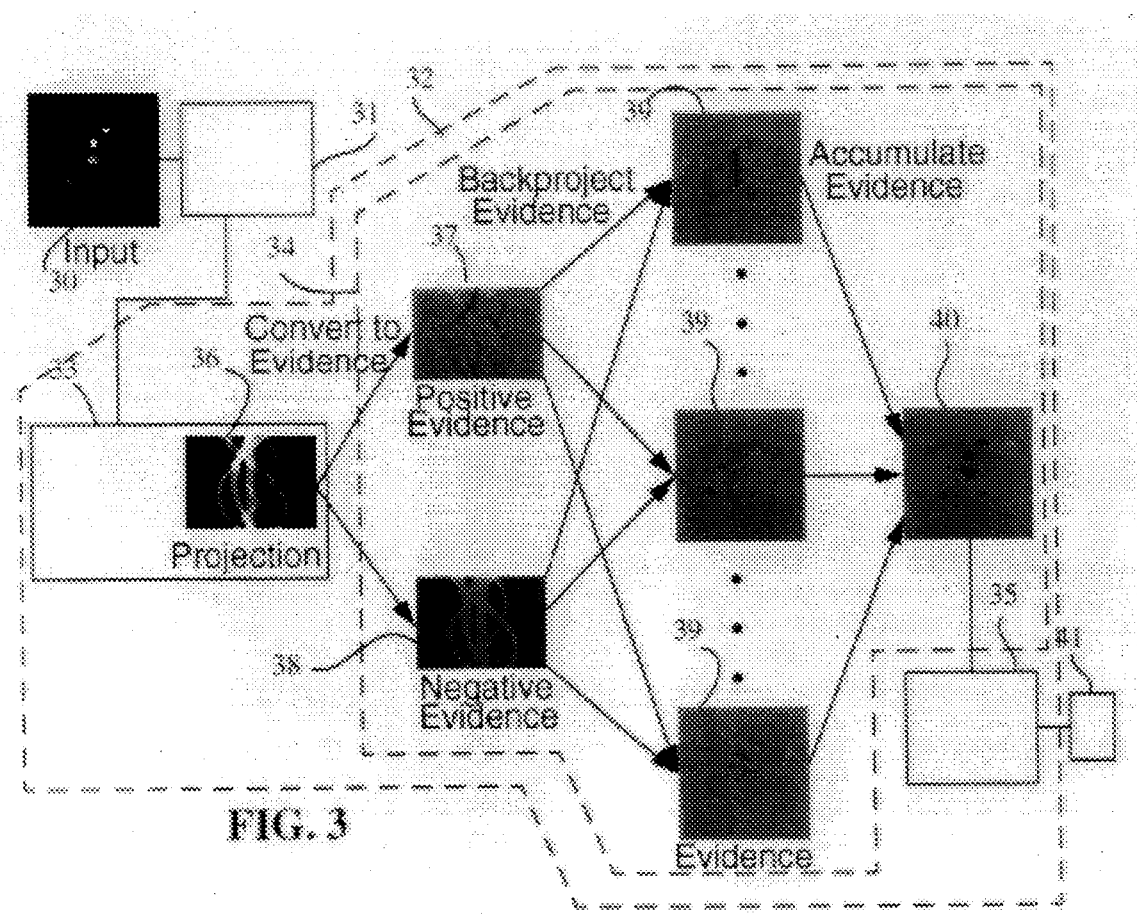
FIG. 3 illustrates a pictorial overview of the evidential reconstruction system of the present invention.

FIG. 3 shows a pictorial overview of the reconstruction process (in two dimensional). As shown here, the input 30 actually represents the patient (12 of FIG. 1) which provides an input to the x-ray angiographic equipment 31. The x-ray angiographic equipment 31 is connected to a computer 32 which comprises the acquisition component 33, the reconstruction component 34 and the display measurement component 35. The acquisition component 33 utilizes the x-ray angiographic equipment 31 and acquires the mask series and the contrast series. The mask series is then subtracted from the contrast series and projection images 36 are obtained. The reconstruction component 34 then recreates the geometry of the vasculature based on the projection images 36 gathered by the acquisition component 33. The reconstruction component 34 starts by converting the grey scale values of the projection images 36 (digital subtraction angiogram) into positive evidence 37 and negative evidence 38. The positive evidence 37 and the negative evidence 38 are then backprojected 39 along the projection ray and accumulated 40 by using the D-S theory. The accumulated evidence 40 which is the results of the reconstruction component 34 then enters the display measurement component 35 which renders the final belief volume using standard technology. The final belief volume is then displayed on a video screen 41 or used for measuring specific physiological parameters.

Figure 4:
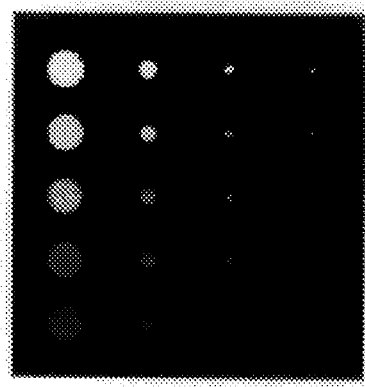
FIGS. 4, 5 and 6 illustrate the results of the present invention without iterations with FIG. 4 showing the input phantom, FIG. 5 showing the sinogram and FIG. 6 showing the results of the reconstruction.
Figure 5:
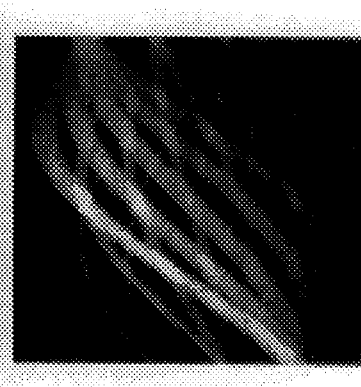
Figure 6:

An evidential reconstruction of a dynamic two dimensional computer phantom is shown in FIGS. 4, 5 and 6. The dynamics of the contrast bolus have been simulated by making the structures in the phantom fade in and out over the course of the projection sequence. Structures in each row have the same intensity and fade in and out simultaneously. However, the intensity values of the structures and their timing varies from row to row. FIG. 4 shows the original phantom with all of the structures at their maximum intensity. FIG. 5 shows the projection sinogram; it consists of 60 images taken over 180 degrees using fan beam geometry. FIG. 6 shows the results of evidential reconstruction. Bright areas have greater probability of containing a vessel. Notice that the probability of occupancy has been overestimated in much of the background area. The next section describes an iterative extension to ERT that greatly reduces this overestimation of probabilities in background areas.

There is a large family of iterative reconstruction techniques that work by computing the error between the acquired projections and projections of the current volume estimate. Gordon, R., "A Tutorial On ART (algebraic reconstruction techniques)", IEEE Trans. on Nuclear Science, Vol. 21, 1974; Herman, G. T., and Lent, A., "Iterative Reconstruction Algorithms", Comput. Biol. Med., Vol. 6, 1976. The volume estimate is then updated based on this error measure. However, one can not compute the projection errors for dynamic scenes because the projections are only valid for a specific point in time. Because it is not possible to use the projection errors to update the estimated volume, another paradigm is needed.

ERT's iterative technique varies the distribution of the evidence along the projection ray based on results from previous iterations. Voxels with high belief in the previous iteration receive a greater portion of positive evidence than voxels with smaller belief in the previous iteration. They also receive a smaller portion of negative evidence than voxels with smaller belief in the previous iteration. This updating scheme encourages convergence because voxels with high belief in the previous iteration receive more positive evidence in the current iteration, and voxels with low belief in the previous iteration receive more negative evidence in this iteration. The belief-weighted update functions for a projection, j, are shown below:

$$m_{voxel\ (i)}(\{occ\}) = m_{proj\ (j)}(\{occ\})\ (w_{ij}Bel_{voxel\ (i)}(\{occ\}))/\Sigma_k w_{kj}Bel_{voxel\ (k)}(\{occ\}))$$

$$m_{voxel(i)}(\{unocc\}) = \qquad (13)$$

$$m_{proj(j)}(\{unocc\})((w_{ij}(1 - Bel_{voxel(i)}(\{occ\})))/\Sigma_k w_{kj}(1 - Bel_{voxel(k)}(\{occ\})))$$

$$m_{voxel\ (i)}(\theta) = 1 - m_{voxel\ (i)}(\{occ\}) - m_{voxel\ (i)}(\{unocc\})$$

Where $Bel(\Psi)$ is the belief in $\Psi$ from the previous iteration. Note that these equations are equivalent to the original backprojection equations if the belief functions for all of the voxels of usinal. Thus, instead of using the original equations for the first iteration and the modified equations for the subsequent iterations, we initialize all of the voxels in the belief volume to 0.5 and use the modified equations for all of the iterations.

The final system requires that three volumes be maintained in memory: one to hold $Bel(\{occ\})$ from the previous iteration, and two to hold $m(\{occ\})$ and $m(\{unocc\})$ for the current iteration. The following pseudo-code gives the final reconstruction system:

Step 1) Initialize $Bel(\{occ\})$ such that all voxels=0.5.

Step 2) Convert pixel values in the projection images to projection belief functions (BPAs).

Step 3) For each projection, update $m(\{occ\})$ and $m(\{unocc\})$ by backprojecting the evidence in the projection BPAs using belief weighting.

Step 4) After all of the projections have been backprojected, copy $m(\{occ\})$ into $Bel(\{occ\})$ because the belief of a singleton is equal to its probability mass.

Step 5) Stop if an iteration count reaches a preset limit; otherwise, go to Step 3.

Note that a major difference between the evidential reconstruction technique and other iterative reconstruction methods is that the input to the pack-projection step (the projection BPAs) of the present invention is constant from iteration to iteration. What changes between iterations is how this data is distributed along the projection ray because it is weighted based on previous belief values. This procedure is different from the other iterative techniques that change the input to the backprojection step (i.e. the projection error), but distribute this data the same in every step of the iteration.

Figure 7:
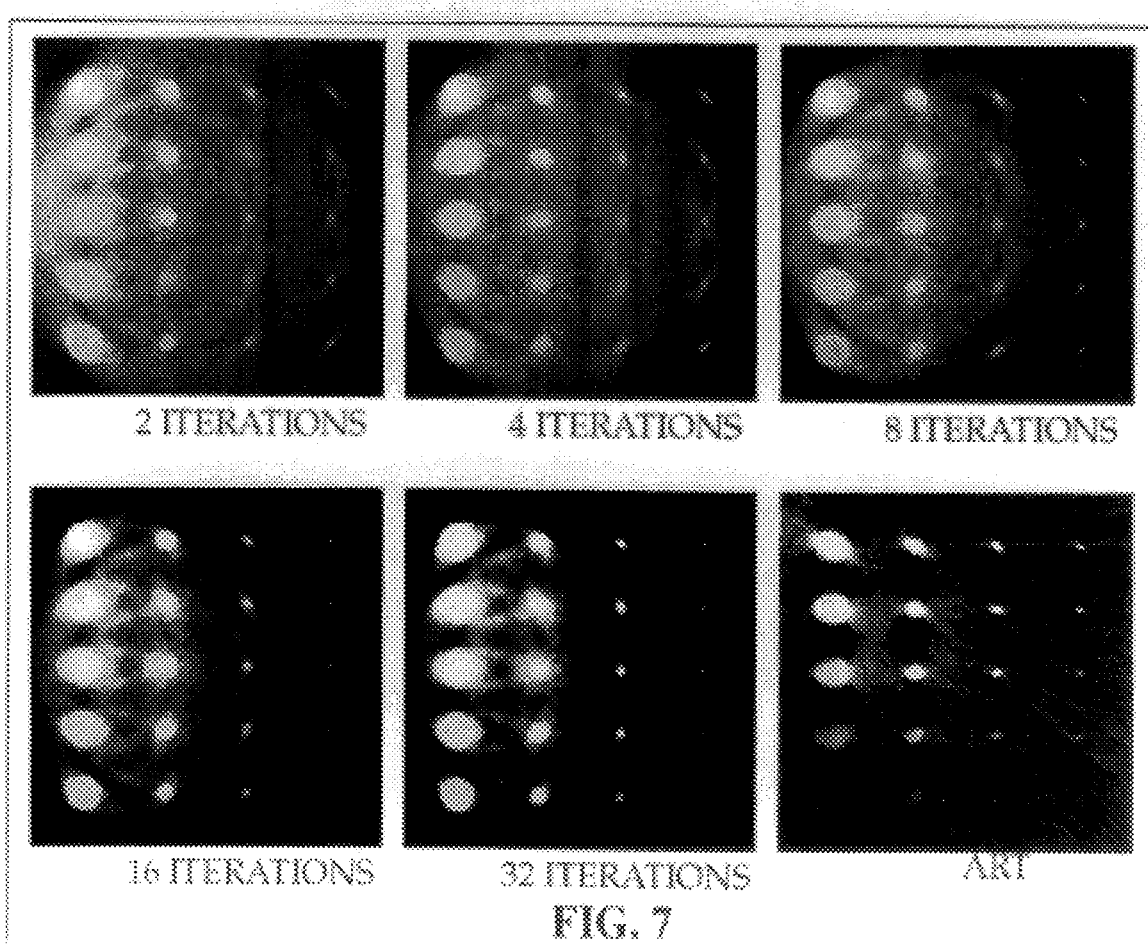
FIG. 7 illustrates the results of iterative evidential reconstruction on the dynamic phantom illustrated in FIG. 4. Results are shown for 2, 4, 8, 16 and 32 iterations and for ART reconstruction.

FIG. 7 shows the results of the evidential reconstruction technique for the previous dynamic phantom example for 2, 4, 8, 16 and 32 iterations and for the results produced by ART for the same phantom. As can be seen here, the iterative procedure is able to concentrate the evidence to increase the belief in voxels containing the structures and decrease the belief in the background voxels. Furthermore, the present invention is able to recover all of the structures, while ART is unable to recover the dimmest structures.

Figure 8:
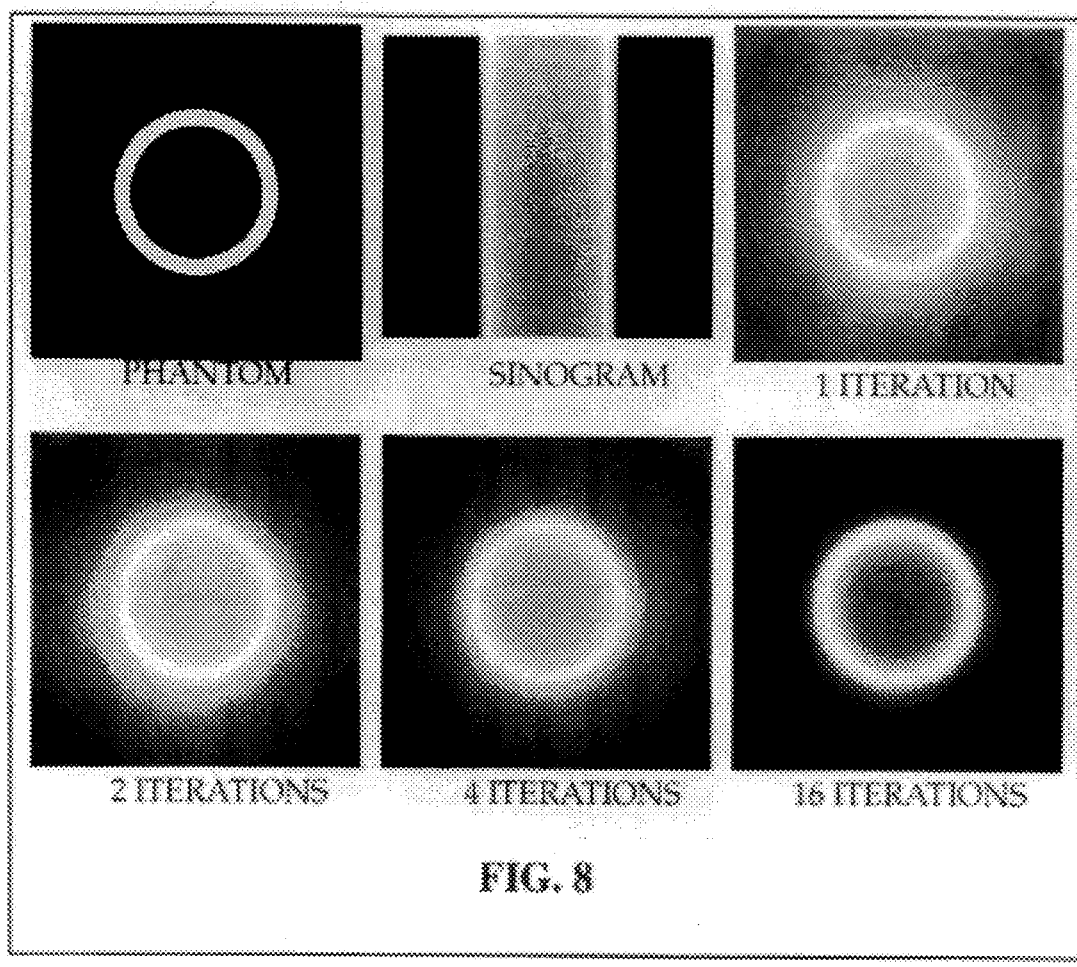
FIG. 8 illustrates the results of iterative evidential reconstruction on a static two dimensional ring with the original phantom, its sinogram, and the results for 1, 2, 4, and 16 iterations shown.

The evidential reconstruction of a two dimensional ring from 60 fan-beam projections over 180 degrees is shown in FIG. 8. This phantom illustrates that the reconstruction process can delineate the background region in the center of the ring even though no viewpoint gives an unobstructed view of this region. This example is meant to show that the present invention is able to reconstruct multiple structure/ background regions correctly even if some structures are obstructed in all projections.

There are a number of ways that the computational efficiency of the present invention can be improved. The most success has been found by segmenting the projections to exclude sections from the active computation area. Since the segmentation is used only to improve the computation speed, a precise segmentation is not required. All that is needed is to know those areas in which a vessel is known not to be present. The remaining areas may or may not contain vessels.

It is also possible to improve the computational speed by excluding sections of the volume from the active computation if it is known that these sections do not contain any vessels. These volumes of interest can be computed by identifying projections in which the vessel tree has been saturated with contrast material. The segmented vessels from these projections are then backprojected into the volume and their intersections found to produce the volume of interest. Once again, a precise segmentation is not needed because it is only used to improve the computation speed.

Other acceleration techniques are possible. For example, hierarchical reconstruction could be used to reconstruct the gross structures in the first iterations and then move to the finer structures in the latter iterations as has been done with ART. Saint-Felix, D., Trousset, Y., Picard, C., and Rougee, A., "3D Reconstruction of High Contrast Objects Using a Multi-scale Detection/Estimation Scheme", 3D Imaging in Medicine, Springer-Verlag, 1990. Also, a large portion of the computation time is spent computing the pixel weights. Although significant speedups may be possible by using more efficient weight computation methods, other backprojection models can be used that do not require any computation of weights. It is believed that these alternative models offer an efficient implementation of ERT.

As stated earlier, three major aspects of the present invention are the reconstruction of the geometry of the vessels by estimating the probability of occupation over the voxel space rather than physical components. Conversion of projection values into evidence (probability estimate) and then backprojecting the evidence through the volume. And, third, the use of the Dempster-Shafer Theory to combine information from other sources.

It is not intended that the present invention be limited to the hardware or software arrangement, or operational procedures shown disclosed. This invention includes all of the alterations and variations thereto as encompassed within the scope of the claims as follows.

I claim:

1. A system for evidential reconstruction of vessel trees from x-ray angiograms with a dynamic contrast bolus comprising:

x-ray angiographic equipment means capable of producing x-ray angiograms; and, computer means connected to said x-ray angiographic equipment means;

wherein said computer means comprises:

acquisition means connected to said x-ray angiographic equipment means;

reconstruction means connected to said acquisition means; and, display/measurement means connected to said reconstruction means.

2. A system for evidential reconstruction of vessel trees from x-ray angiograms with a dynamic contrast bolus as claimed in claim 1 further comprising: video display means connected to said computer means.

3. A system for evidential reconstruction of vessel trees from x-ray angiograms with a dynamic contrast bolus as claimed in claim 1 wherein said acquisition means comprises:

first acquiring means for acquiring a mask series of DSA;

second acquiring means for acquiring a contrast series of DSA;

subtraction means for subtracting said mask series from said contrast series; and, creation means for creating a DSA sequence.

4. A system for evidential reconstruction of vessel trees from x-ray angiograms with a dynamic contrast bolus as claimed in claim 1 wherein said reconstruction means comprises:

recreation means for recreating geometry of said vessel trees based on projection images gathered by said acquisition means by estimating probability of occupation over a voxel space.

5. A system for evidential reconstruction of vessel trees from x-ray angiograms with a dynamic contrast bolus as claimed in claim 4 wherein said recreation means comprises:

conversion means for converting an angiographic series into belief functions;

initialization means for initializing said belief functions to indicate complete ignorance;

starting means for starting iterative procedure with data being projected from said belief functions;

backprojection means for backprojecting evidence through a volume; and, accumulating means for accumulating said backprojected evidence by using Dempster-Shafer theory.

6. A system for evidential reconstruction of vessel trees from x-ray angiograms with a dynamic contrast bolus as claimed in claim 2 wherein said display/measurement means comprises:

a first system for displaying volumetric data on said video display means; and, a second system for measuring specific physiological parameters from said volumetric data.

7. A system for evidential reconstruction of vessel trees from x-ray angiograms with a dynamic contrast bolus as claimed in claim 1 wherein said acquisition means comprises:

acquiring means for acquiring an angiographic series;

estimating means for establishing a DSA mask series from said angiographic series; and, subtraction means for subtracting said mask series from said angiographic series.

8. A system for evidential reconstruction of vessel trees from x-ray angiograms with a dynamic contrast bolus as claimed in claim 1 wherein said acquisition means comprises:

acquiring means for acquiring an angiographic series.

9. A system for evidential reconstruction of vessel trees from x-ray angiograms with a dynamic contrast bolus as claimed in claim 2 wherein said display/measurement means comprises:

a system for displaying volumetric data on said video display means.

10. A system for evidential reconstruction of vessel trees from x-ray angiograms with a dynamic contrast bolus as claimed in claim 1 wherein said display/measurement means comprises:

a system for measuring specific physiological parameters from said volumetric data.

11. A system for evidential reconstruction of vessel trees from x-ray angiograms with a dynamic contrast bolus comprising:

x-ray angiographic equipment capable of producing x-ray angiograms;

a computer connected to said x-ray angiographic equipment; and, a video display connected to said computer;

wherein said computer comprises:

an acquisition component connected to said x-ray angiographic equipment;

a reconstruction component connected to said acquisition component; and, a display/measurement component connected to said reconstruction component.

12. A system for evidential reconstruction of vessel trees from x-ray angiograms with a dynamic contrast bolus as claimed in claim 11 wherein said acquisition component comprises:

first acquiring means for acquiring a mask series of DSA;

second acquiring means for acquiring a contrast series of DSA;

subtraction means for subtracting said mask series from said contrast series; and, creation means for creating a DSA sequence.

13. A system for evidential reconstruction of vessel trees from x-ray angiograms with a dynamic contrast bolus as claimed in claim 12 wherein said reconstruction component comprises:

conversion means for converting an angiographic series into belief functions;

initialization means for initializing said belief functions to indicate complete ignorance;

starting means for starting iterative procedure with data being projected from said belief functions;

decision means for deciding whether stop criteria has been met wherein if said stop criteria has not been met, said starting means starts said iterative procedure again;

backprojection means for backprojecting evidence through a volume; and, accumulation means for accumulating backprojected evidence.

14. A system for evidential reconstruction of vessel trees from x-ray angiograms with a dynamic contrast bolus as claimed in claim 13 wherein said display/measurement component comprises:

a first system for displaying volumetric data on said video display means; and, a second system for measuring specific physiological parameters from said volumetric data.

15. A system for evidential reconstruction of vessel trees from x-ray angiograms with a dynamic contrast bolus as claimed in claim 11 wherein said acquisition component comprises:

acquiring means for acquiring an angiographic series;

estimating means for establishing a DSA mask series from said angiographic series; and, subtraction means for subtracting said mask series from said angiographic series.

16. A method for evidential reconstruction of vessel trees from x-ray angiograms with a dynamic contrast bolus comprising the steps of:

utilizing x-ray angiographic equipment to produce xray angiograms; and, utilizing computer means connected to said x-ray angiographic equipment means;

wherein utilizing said computer means comprises the steps of:

acquiring a mask series of DSA;

acquiring a contrast series of DSA;

subtracting said mask series from said contrast series;

creating a DSA sequence;

recreating a geometry of vasculature, based on projection images gathered, by estimating probability of occupation over a voxel space.

17. A method for evidential reconstruction of vessel trees from x-ray angiograms with a dynamic contrast bolus as claimed in claim 16 wherein recreating a geometry of vasculature based on projection images gathered comprises the steps of:

converting an angiographic series into belief functions;

initializing said belief functions to indicate complete ignorance;

starting iterative procedure with data being projected from said belief functions;

backprojecting evidence; and, accumulating backprojected evidence by using Dempster-Shafer theory.

18. A method for evidential reconstruction of vessel trees from x-ray angiograms with a dynamic contrast bolus as claimed in claim 17 further comprising the step of:

deciding whether stop criteria has been met, wherein if said stop criteria has not been met, starting iterative procedure again.

19. A method for evidential reconstruction of vessel trees from x-ray angiograms with a dynamic contrast bolus as claimed in claim 17 further comprising the step of:

displaying volumetric data on a video display means.

20. A method for evidential reconstruction of vessel trees from x-ray angiograms with a dynamic contrast bolus as claimed in claim 19 further comprising the step of:

measuring specific physiological parameters from said volumetric data.

* * * * *